United States Patent
Ranchod et al.

(10) Patent No.: US 10,448,828 B2
(45) Date of Patent: Oct. 22, 2019

(54) MULTIPLE OFF-AXIS CHANNEL OPTICAL IMAGING DEVICE WITH ROTATIONAL MONTAGE

(71) Applicant: BROADSPOT IMAGING CORP, Richmond, CA (US)

(72) Inventors: Tushar M. Ranchod, Berkeley, CA (US); Benjamin A. Jacobson, Santa Barbara, CA (US); Andre E. Adams, Tiburon, CA (US)

(73) Assignee: BROADSPOT IMAGING CORP, Richmond, CA (US)

( * ) Notice: Subject to any disclaimer, the term of this patent is extended or adjusted under 35 U.S.C. 154(b) by 0 days.

(21) Appl. No.: 16/224,208

(22) Filed: Dec. 18, 2018

(65) Prior Publication Data

US 2019/0200860 A1 Jul. 4, 2019

Related U.S. Application Data

(60) Provisional application No. 62/611,069, filed on Dec. 28, 2017.

(51) Int. Cl.
  *A61B 3/00* (2006.01)
  *A61B 3/12* (2006.01)
  *A61B 3/14* (2006.01)

(52) U.S. Cl.
  CPC .............. *A61B 3/14* (2013.01); *A61B 3/0058* (2013.01); *A61B 3/12* (2013.01)

(58) Field of Classification Search
  CPC ....... A61B 3/14; A61B 3/0025; A61B 3/0058; A61B 3/10; A61B 3/12;
  (Continued)

(56) References Cited

U.S. PATENT DOCUMENTS 6,141,034 A * 10/2000 McCutchen ........... G02B 27/22
                                                                         348/36
7,140,730 B2    11/2006 Wei et al.
(Continued)

OTHER PUBLICATIONS

Götzinger et al. "Polarization maintaining fiber based ultra-high resolution spectral domain polarization sensitive optical coherence tomography" Opt. Express, vol. 17(25), pp. 22704-22717; Dec. 7, 2009.

(Continued)

*Primary Examiner* — Jordan M Schwartz
(74) *Attorney, Agent, or Firm* — Maschoff Brennan (57) ABSTRACT

An optical imaging device may include a support structure and imaging channels, where each imaging channel may include a discrete optical imaging pathway. The optical imaging device may also include image capturing devices respectively associated with one of the imaging channels to capture a first set of digital photograph images of respective portions of the eye. In some embodiments, the first set of digital photograph images may overlap each other and may be stitched together such that the first set of digital photograph images form a first composite image with a first set of scallops. Additionally, the optical imaging device may be rotated to capture a second set of digital photograph images that overlap each other and may be stitched together such that the second set of digital photograph images form a second composite image with a second set of scallops positioned differently than the first set of scallops.

20 Claims, 8 Drawing Sheets

(58) Field of Classification Search
CPC ......... G06T 2207/20221; G06T 3/4038; G06T 7/11; G06K 9/34; G06K 2009/2045; G02B 21/367; H04N 5/23238
USPC ....................................................... 351/206
See application file for complete search history.

(56) References Cited

U.S. PATENT DOCUMENTS

| | | |
|---|---|---|
| 7,854,510 B2 | 12/2010 | Verdooner et al. |
| 8,714,743 B2 | 5/2014 | Verdooner |
| 8,807,751 B2 | 8/2014 | Kahn et al. |
| 9,295,388 B2 | 3/2016 | Lawson et al. |
| 9,314,155 B2 | 4/2016 | Verdooner |
| 9,480,394 B2 | 11/2016 | Verdooner |
| 9,521,950 B2 | 12/2016 | Verdooner |
| 2009/0153796 A1 | 6/2009 | Rabner |
| 2010/0195048 A1 | 8/2010 | Hammer et al. |
| 2011/0234978 A1 | 9/2011 | Hammer et al. |
| 2012/0249957 A1 | 10/2012 | Shibata et al. |
| 2012/0287255 A1 | 11/2012 | Ignatovich et al. |
| 2013/0107277 A1 | 5/2013 | Hirose et al. |
| 2013/0250243 A1 | 9/2013 | Cech |
| 2013/0258044 A1* | 10/2013 | Betts-Lacroix ...... H04N 13/243 348/36 |
| 2013/0271728 A1 | 10/2013 | Ranchod |
| 2013/0271729 A1 | 10/2013 | Ranchod |
| 2014/0226128 A1 | 8/2014 | Lawson et al. |
| 2015/0173613 A1* | 6/2015 | Gerrans ................... A61B 3/14 351/206 |
| 2015/0288865 A1* | 10/2015 | Osborne .............. H04N 5/2624 348/218.1 |
| 2016/0135679 A1 | 5/2016 | Frisken et al. |
| 2016/0205298 A1* | 7/2016 | Zhou ........................ A61B 3/12 348/78 |
| 2016/0367135 A1* | 12/2016 | Myung .................. A61B 3/145 |
| 2017/0314908 A1 | 11/2017 | Chong |
| 2019/0038132 A1* | 2/2019 | Lai ....................... A61B 3/0008 |

OTHER PUBLICATIONS

International Search Report dated Mar. 5, 2019 as received in Application No. PCT/US2018/067398.
Written Opinion of the International Searching Authority dated Mar. 5, 2019 as received in Application No. PCT/US2018/067398.

* cited by examiner

MULTIPLE OFF-AXIS CHANNEL OPTICAL IMAGING DEVICE WITH ROTATIONAL MONTAGE

FIELD

The application relates generally to a multiple off-axis channel optical imaging device with rotational montage.

BACKGROUND

Ocular imaging is commonly used both to screen for diseases and to document findings discovered during clinical examination of the eye. Specifically, documentation and analysis of optical imaging may be relevant to comprehensive eye examinations and full evaluations of current conditions, treatment, and/or early prevention of various eye conditions and diseases. However, complete or near-complete imaging of portions of the eye, such as the retina, with digital photography may be a challenging task.

The subject matter claimed herein is not limited to embodiments that solve any disadvantages or that operate only in environments such as those described above. Rather, this background is only provided to illustrate one example technology area where some embodiments described herein may be practiced.

SUMMARY

Embodiments of the disclosure discuss an optical imaging device. The optical imaging device may include a support structure and imaging channels, where each imaging channel may include a discrete optical imaging pathway. Additionally, the imaging channels disposed within the support structure may be aimed at different angles relative to each other such that each optical imaging pathway is directed through a pupil of the eye towards corresponding partially overlapping regions of a retina.

The optical imaging device may also include image capturing devices respectively associated with one of the imaging channels to capture a first set of digital photograph images of respective portions of the eye. In some embodiments, the first set of digital photograph images may overlap each other and may be stored in a storage device of the optical imaging device for stitching together such that the first set of digital photograph images form a first composite image with a first set of scallops. Additionally, the optical imaging device may be configured to be rotated to capture a second set of digital photograph images that overlap each other and may be stored in the storage device of the optical imaging device for stitching together such that the second set of digital photograph images form a second composite image with a second set of scallops positioned differently than the first set of scallops.

The objects and advantages of the embodiments will be realized and achieved at least by the elements, features, and combinations particularly pointed out in the claims.

Both the foregoing general description and the following detailed description are given as examples and are explanatory and are not restrictive of the invention, as claimed.

BRIEF DESCRIPTION OF THE DRAWINGS

Example embodiments will be described and explained with additional specificity and detail through the use of the accompanying drawings in which.

DESCRIPTION OF EMBODIMENTS

In some embodiments of the present disclosure, imaging channels, each with at least one unique imaging pathway, may approach the eye at different angles. The respective imaging pathways may cross each other within the plane of the iris of the human eye, or within the space between the cornea and the mid-vitreous cavity, or at any point between the retina and the cornea. In these or other embodiments, none of the imaging channels may be coaxial with a central axis of the eye. However, in some embodiments, at least one imaging channel may be coaxial with the central axis of the eye. The imaging channels may image different but partially overlapping regions of the eye such that the resulting images can be stitched into a single composite optical image with a combined area greater than any constituent image and in such a way that gaps may not appear within the composite image. For example, a first image may correspond to a first optical region; a second image may correspond to a second optical region; and a third image may correspond to a third optical region. In this example, each region may be overlapped by at least one other region. Continuing with the example, the three example images may be gathered, and the overlap regions may be averaged or homogenized for clarity and continuity thereby helping to create a single contiguous image of all three regions based on the three individual images. In these or other embodiments, images (whether individual images or composite images) may be stored in a storage device coupled to the optical imaging device. In these or other embodiments, more or fewer than three images may comprise a composite image.

In some embodiments, the composite image may have an irregular outer contour as defined by scalloped regions or un-imaged regions that are beyond the field of view of the optical imaging device. Thus, in some embodiments, the optical imaging device may include imaging channels that can be rotated relative to the eye and a second multi-image acquisition may be performed to generate a different composite image of the eye with a similar contour to the composite image but with scallops located in different positions than in the primary (non-rotated) composite image. In these or other embodiments, the primary and rotated composite images may be stitched together to generate a super-montaged image covering more optical surface area, e.g., of a retina, than either the primary or the rotated composite images individually.

Figure 1A:
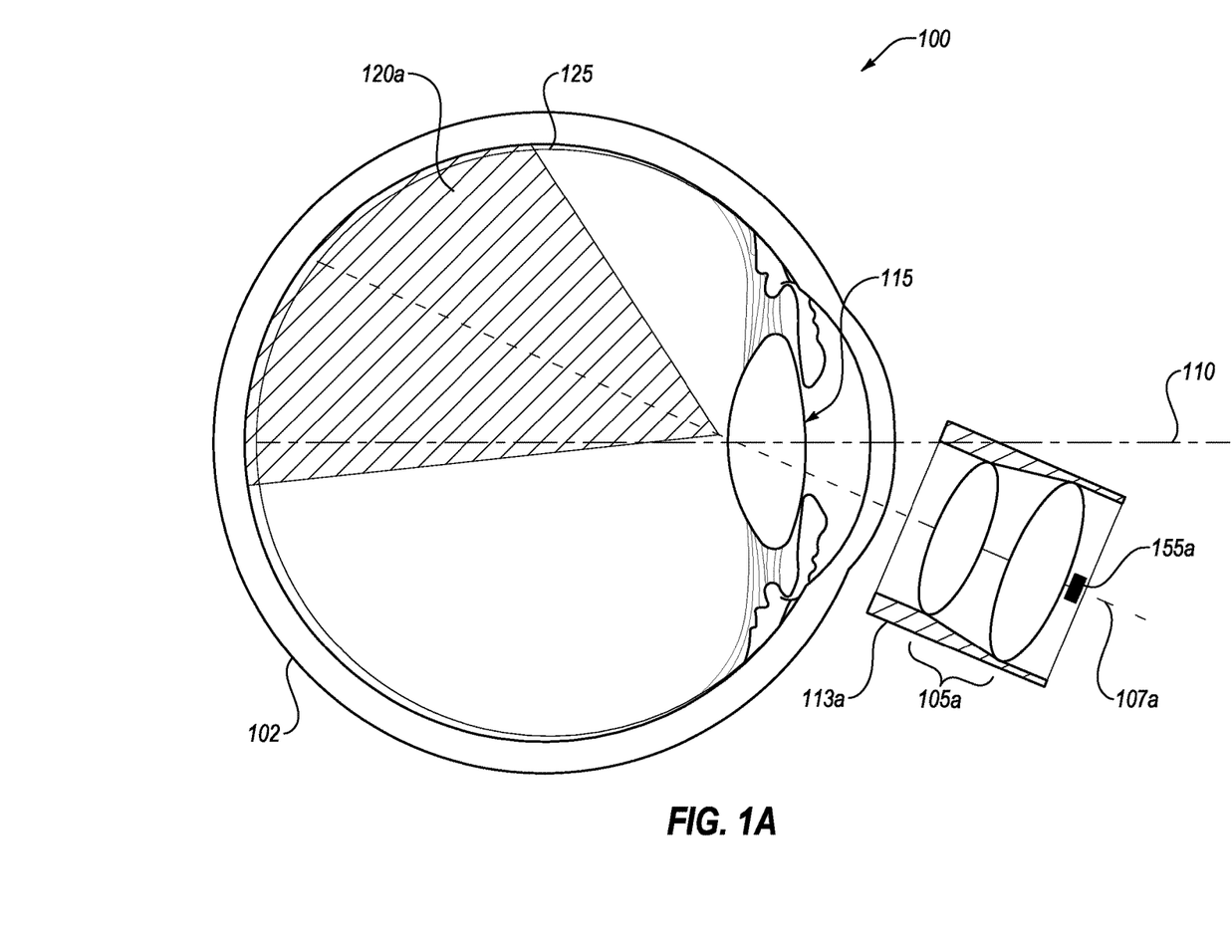
FIG. 1A illustrates a cross-sectional side view of an eye, including an example optical imaging pathway for imaging the eye.
Figure 1B:
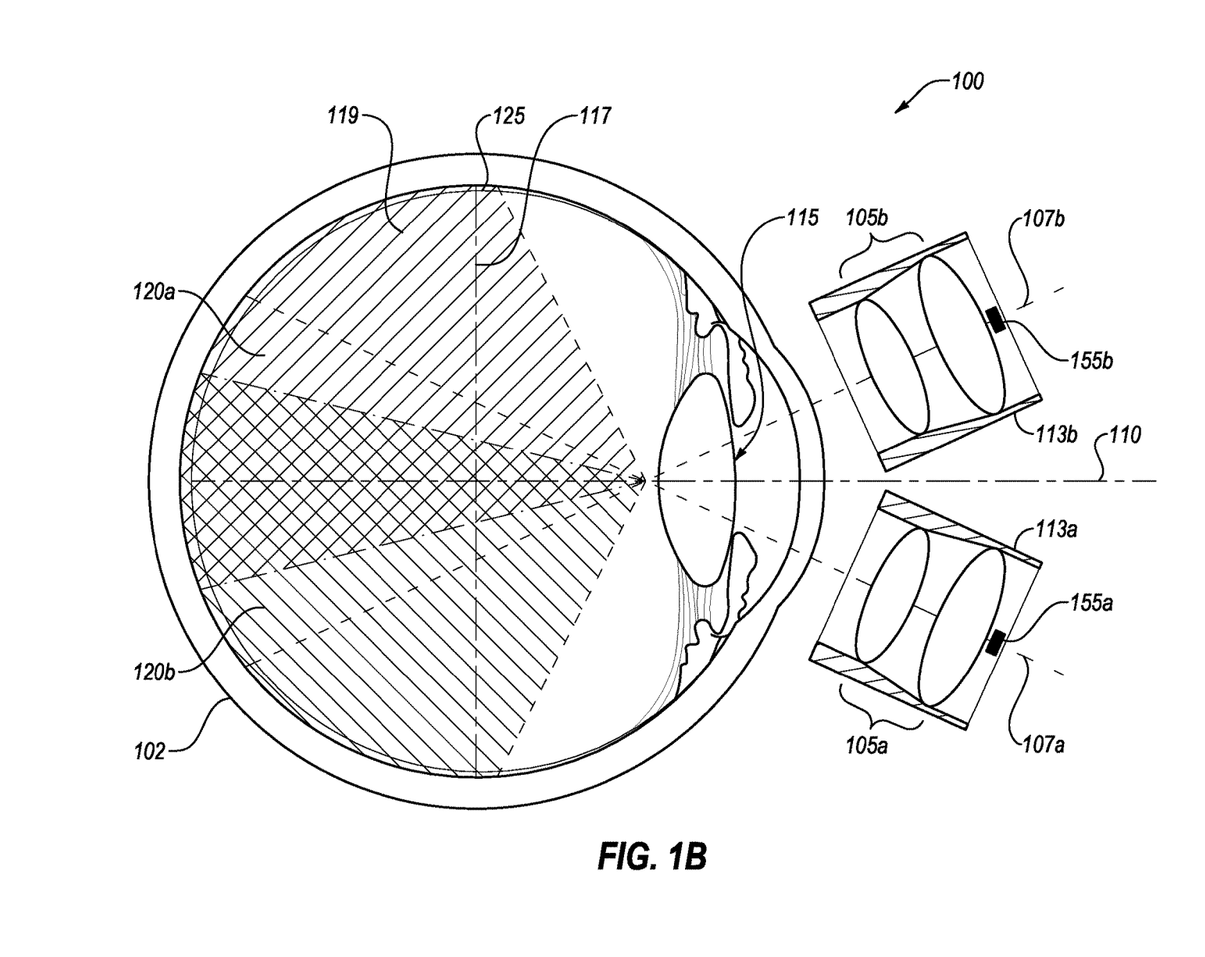
FIG. 1B illustrates another cross-sectional side view of the eye of FIG. 1A, including multiple example optical imaging pathways for imaging the eye.
Figure 1C:
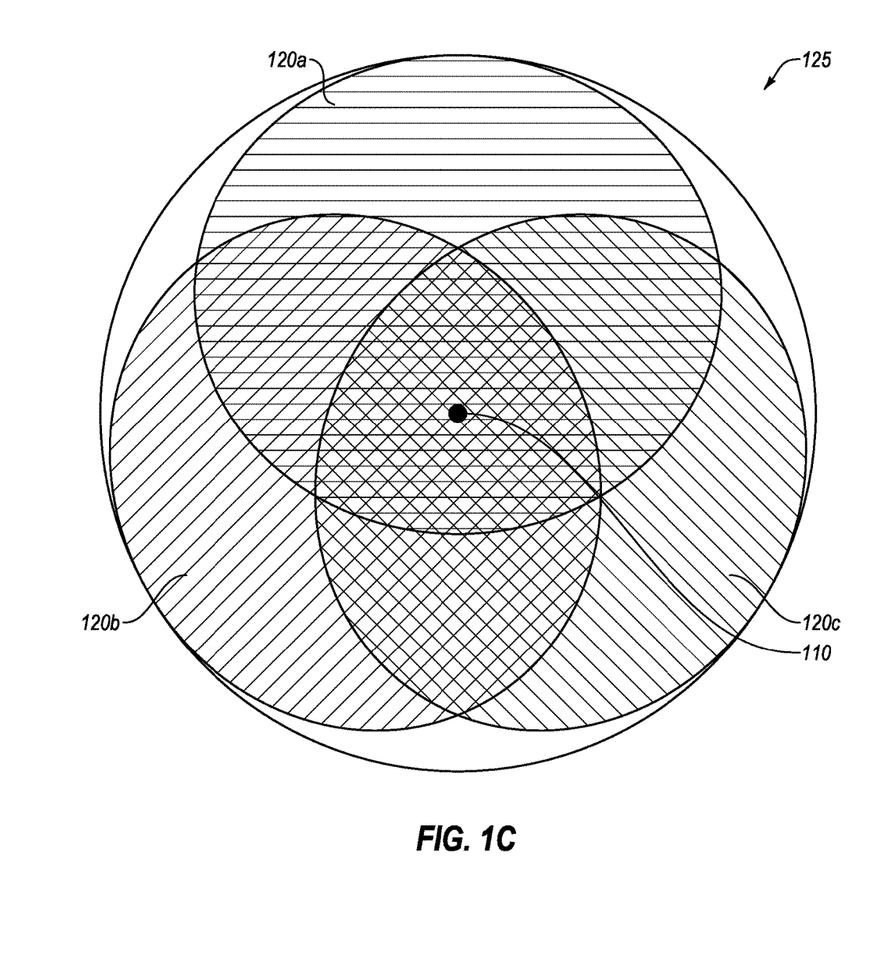
FIG. 1C illustrates a cross-sectional front view of the eye of FIG. 1A, including multiple overlapping imaging regions of the eye.

FIGS. 1A-1C indicate an example progression for achieving a composite optical image. For example, FIG. 1A illustrates a cross-sectional side view of an eye 102, including an example optical imaging pathway 107a for imaging the eye 102. FIG. 1B illustrates the same cross-sectional side view of the eye 102 with the addition of a second example optical imaging pathway 107b for imaging the eye 102. FIG. 1C illustrates three overlapping imaging regions 120a, 120b, and 120c for imaging an example area of the eye 102, including a retina 125. FIG. 1A also illustrates an imaging channel 113a, an eye lens 115, optical lenses 105a, a central axis 110, an imaging region 120a, and an image capturing device 155a. In these or other embodiments, the optical imaging pathway 107a may proceed from within the imaging channel 113a of a device (such as the device 200/300 illustrated in FIGS. 2A/2B and FIG. 3), through the pupil and the eye lens 115, and to the retina 125. Additionally or alternatively, the optical imaging pathway 107a may start and/or end at the image capturing device 155a, and the image capturing device 155a may be positioned anywhere within the imaging channel 113a. For example, the imaging capturing device 155a may be positioned between the optical lenses 105a, along a central axis of the imaging channel 113a normal to the eye 102, and/or off the central axis of the imaging channel 113a normal to the eye 102. In these or other embodiments, the optical imaging pathway 107a may be a center axis of a field of view of the image capturing device 155a.

Additionally or alternatively, the imaging region 120a may correspond to the optical imaging pathway 107a. For example, an area of the retina 125 that is covered by or is adjacent to the optical imaging pathway 107a may define the metes and bounds of the imaging region 120a. In other embodiments, other areas of the eye 102, such as the cornea, the iris, the iridocorneal angle, the sclera, and any other suitable area of the eye 102, whether in the anterior or posterior chamber of the eye 102, may be imaged.

In some embodiments, the optical lenses 105a may be housed by the imaging channel 113a and may collimate illumination light proceeding through the imaging channel 113a such that the illumination light proceeds collinear with and/or parallel to the optical imaging pathway 107a and illuminates at least a portion of the imaging region 120a. In some embodiments, the optical lenses 105a may be sized and shaped to fill an inner diameter of the imaging channel 113a that houses the optical lenses 105a, while in other embodiments, the optical lenses 105a may be sized and shaped to be less than the inner diameter of the imaging channel 113a. Additionally or alternatively, the optical lenses 105a may focus, disperse, and/or otherwise alter light transmission to enhance imaging capability of the image capturing device 155a to image the imaging region 120a. In these or other embodiments, the image capturing device 155a may be an imaging device or sensor that may respectively include an entire imaging sensor or a portion of a larger digital camera, where the larger digital camera may be positioned outside of the optical imaging device.

In some embodiments, other optical elements may also be included within the imaging channel 113a. For example, a prism may be positioned anywhere within the imaging channel 113a, e.g., between the optical lenses 105a, at a distal end of the imaging channel 113a and/or at a proximal end of the imaging channel positioned between the eye 102 and the optical lenses 105a. In some embodiments, the prism may be configured as a mirror, beam splitter, or other suitable reflective element (e.g., partially reflective, substantially reflective, or completely reflective). In these or other embodiments, multiple prisms may be positioned within the imaging channel 113a, while in other embodiments, only a single prism within the imaging channel 113a. In some embodiments, the prism may help direct light to and/or from the eye 102, e.g., permitting multi-directional travel of optical signals between the eye 102 and an optical imaging device. For example, the prism may at least partially direct one or both of the optical imaging pathway 107a and an optical illumination pathway toward the eye 102.

In some embodiments, the optical imaging pathway 107a may not be coaxial to the central axis 110 of the eye 102. In this manner, multiple optical imaging pathways 107 (such as the optical imaging pathways 107a and 107b as shown in FIG. 1B) may enable imaging of the retina 125 and/or other areas of the eye 102, such as the cornea, the iris, the iridocorneal angle, the sclera, and any other suitable area of the eye 102, whether in the anterior or posterior chamber of the eye 102.

Additionally or alternatively, the optical lenses 105a may have fixed or variable positions within the imaging channel 113a. For example, one or more of the optical lenses 105a may be positionally fixed such that the optical lenses 105a may not move within the imaging channel 113a. As another example, one or more of the optical lenses 105a may be positionally movable within the imaging channel 113a such that the lenses can slide closer to the eye 102 during examination or slide farther away from the eye 102 during examination. Additionally or alternatively, the optical lenses 105a may be positionally movable within the imaging channel 113a such that the lenses can slide laterally so as to maintain a relative distance between the optical lenses 105a and the eye 102 during examination or image acquisition. Additionally or alternatively, the optical lenses 105a may be fixed positionally, but movable at the fixed position. For example, at least one of the optical lenses 105a may be angularly varied in orientation within the imaging channel 113a such that an angular orientation of the at least one optical lens 105a may be changed to or positioned at any angle such as perpendicular to the optical imaging pathway 107a, parallel to the optical imaging pathway 107a, and any suitable angle therebetween. In this manner, different imaging regions may be obtained and/or optical properties adjusted for lighting and/or imaging.

FIG. 1B illustrates another cross-sectional side view of the eye 102 of FIG. 1A, including multiple example optical imaging pathways 107 (such as the optical imaging pathways 107a and 107b) for imaging the retina 125 and/or other areas of the eye 102, such as the cornea, the iris, the iridocorneal angle, the sclera, and any other suitable area of the eye 102, whether in the anterior chamber or a posterior cavity 119 of the eye 102. Specifically, FIG. 1B shows the addition of an imaging channel 113b, an optical imaging pathway 107b, optical lenses 105b, overlapping imaging regions 120a/120b, and an image capturing device 155b.

The imaging channel 113b, the optical imaging pathway 107b, the optical lenses 105b, and the image capturing device 155b may be the same as or similar to the imaging channel 113a, the optical imaging pathway 107a, the optical lenses 105a, and the image capturing device 155a, respectively, of FIG. 1A. In some embodiments, more or fewer image capturing devices 155 may be utilized in the optical imaging device, e.g., depending on an imaging application or pupil size of the eye to be imaged.

Additionally or alternatively, the imaging channel 113*b* and/or the optical imaging pathway 107*b* may not be coaxial to the central axis 110 of the eye 102. Thus, in some embodiments, the optical imaging pathways 107 of the imaging channels 113 may be angled relative to each other and/or to the central axis 110. For example, in some embodiments, the optical imaging pathways 107 may cross each other at a position within the posterior cavity 119 of the eye 102, and at a position anterior to an equatorial line 117, e.g., when imaging the retina 125. In other embodiments, depending on the desired target area of the eye 102 to be imaged, such as a surface of the cornea, the iris, the iridocorneal angle or the sclera, the optical imaging pathways 107 may converge at a position in the anterior chamber or at a position anterior to an outer surface of the cornea. In other embodiments, depending on the desired target area of the eye 102 to be imaged, the optical imaging pathways 107 may converge at a position in the posterior cavity 119 of the eye 102, and at a position posterior to an equatorial line 117.

In these or other embodiments, the imaging region 120*a* may correspond to the optical imaging pathway 107*a*, and the imaging region 120*b* may correspond to the optical imaging pathway 107*b*. The imaging regions 120*a*/120*b* may include portions of, for example, the retina 125 that are captured in digital images. Additionally or alternatively, the imaging region 120*a* and the imaging region 120*b* may overlap, for example, such that one or more portions of the retina 125 are captured in both images through the imaging channels 113*a* and 113*b*.

In some embodiments, imaging channels 113 may be fixed relative to each other, exactly or approximately, in terms of position in three-dimensional space or in terms of angles relative to a central optical axis of each imaging channel or the central axis 110 of the eye 102. For example, the imaging channels 113 may be angled at approximately equal angles off of the central optical axis of each imaging channel 113. Additionally or alternatively, the imaging channels 113 may be angled at approximately equal angles off of the central axis 110 of the eye 102 of the patient such that the imaging channels 113 may be evenly spaced in the 360 degrees around the central axis 110 of the eye 102 (e.g., each imaging channel 113 offset by approximately 30 degrees to approximately 45 degrees from the central axis 110 of the eye 102 and/or distributed approximately 120 degrees relative to each other).

Figure 3:
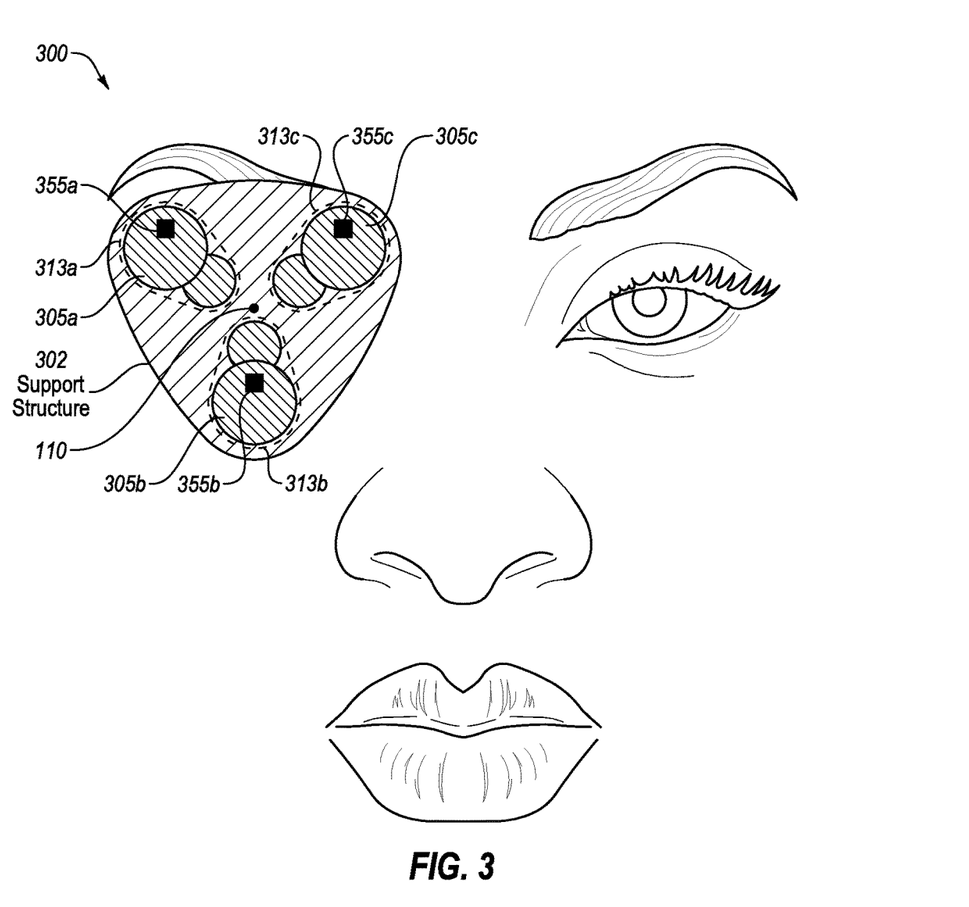
FIG. 3 illustrates a cross-sectional front view of an optical imaging device for imaging the eye, relative to facial features.

In some embodiments, the angles between the imaging channels 113 relative to the central optical axis of each imaging channel 113 or relative to the central axis 110 of the eye 102 may not be equal or consistent. For example, different angles may accommodate different configurations and shapes of facial structures (e.g., a triangular base other than an equilateral triangle may be incorporated). In these or other embodiments, various configurations and numbers of imaging channels 113 may be used. For example, in some embodiments, four or five imaging channels 113 may be used in the optical imaging device 300 (not shown), while in other embodiments, between six and ten imaging channels 113 may be used, while in still other embodiments, only two imaging channels 113 may be used.

In some embodiments, the known relative positioning of the multiple imaging channels 113 may facilitate the stitching of multiple images into a composite image via software analytics. Thus, according to some embodiments, regardless of the angles (equal or not) of the imaging channels 113 relative to the central axis 110 of the eye 102 or relative to the central optical axis of each imaging channel, the angles may be known variables to the software such that image stitching can be achieved with sufficient precision. The multiple images to be stitched into a composite image, which are obtained via the image capturing devices 155 within the imaging channels 113, may be stored in a storage device.

FIG. 1C illustrates a cross-sectional front view of the eye 102 of FIG. 1A, including multiple overlapping imaging regions 120*a*/120*b*/120*c* of the retina 125. In other embodiments, the multiple overlapping imaging regions 120*a*/120*b*/120*c* may correspond to other areas of the eye 102, such as the cornea, the iris, the iridocorneal angle, the sclera, and any other suitable area of the eye 102, whether in the anterior chamber or a posterior cavity 119 of the eye 102. With the three different but overlapping imaging regions 120*a*/120*b*/120*c* of, for example, the retina 125, a composite image may be obtained that includes a combined area with a greater field of view than any single imaging region 120 and with fewer or no gaps within the composite image area. In some embodiments, the central axis 110 of the eye 102 may intersect a position on the retina 125 that is within two or more of the imaging regions 120.

In these or other embodiments of the present disclosure, an optical imaging device (such as that shown in FIG. 3) may include an upside-down pyramidal configuration of imaging channels 113 for increasing a clearance distance relative to facial structures of patients. In other embodiments, additional configurations of the imaging channels 113, other than for an upside-down pyramidal configuration of the optical imaging device, may be implemented. For example, any suitable configuration permitting additional or increased clearance between the optical imaging device and one or both of a bony brow and a nose is contemplated herein. Additionally or alternatively, any suitable configuration permitting multiple imaging channels 113, e.g., two or more imaging channels 113, for imaging the eye 102 may be implemented.

Modifications, additions, or omissions may be made to the embodiments of FIGS. 1A-1C without departing from the scope of the present disclosure. For example, in some embodiments, the channels 113*a*/113*b* may include any number of other components that may not be explicitly illustrated or described. Additionally or alternatively, for example, the imaging regions 120*a*/120*b*/120*c* may include different sizes, shapes, overlapping areas, etc. than may be explicitly illustrated or described.

Figure 2A:
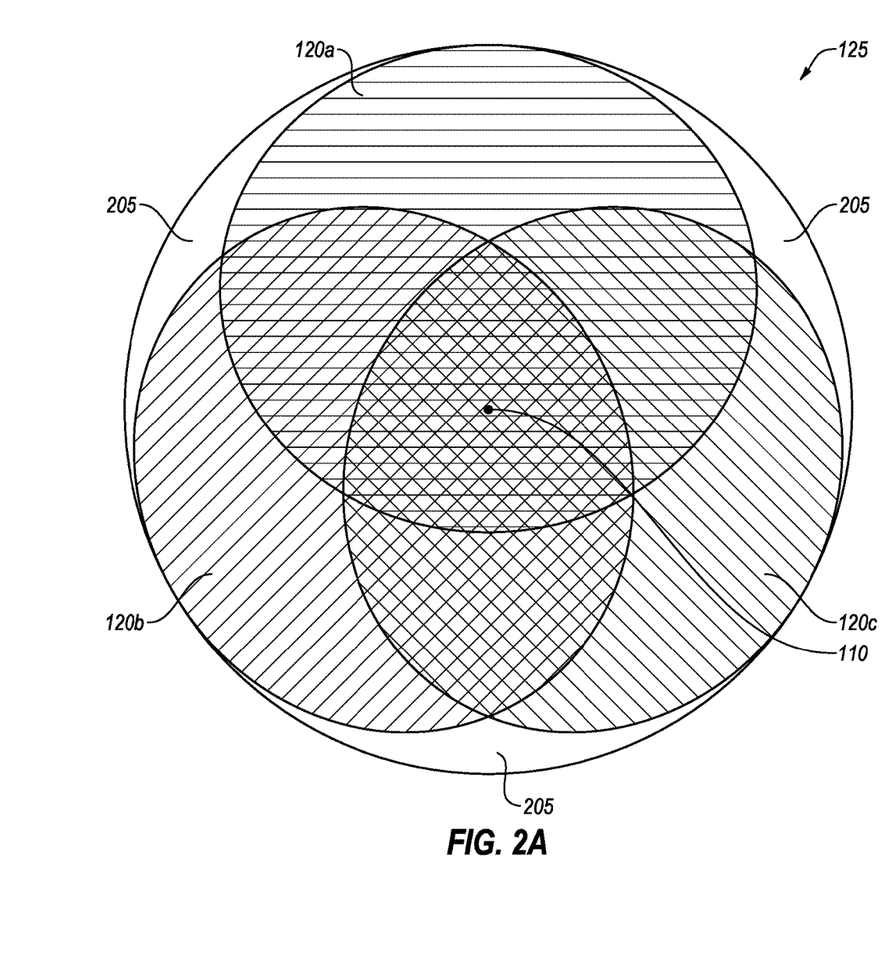
FIG. 2A illustrates a cross-sectional front view of the eye of FIG. 1A, including an example set of multiple overlapping imaging regions of the eye.
Figure 2B:
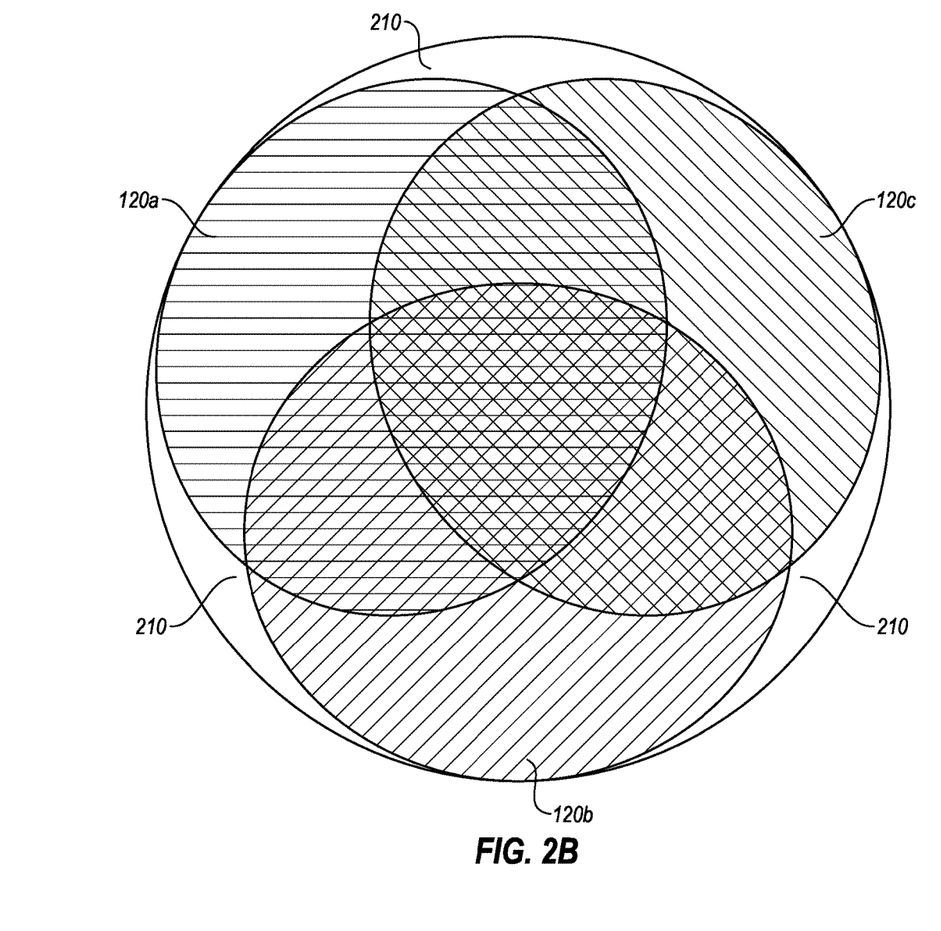
FIG. 2B illustrates a cross-sectional front view of the eye of FIG. 1A, including another example set of multiple overlapping imaging regions of the eye.
Figure 2C:
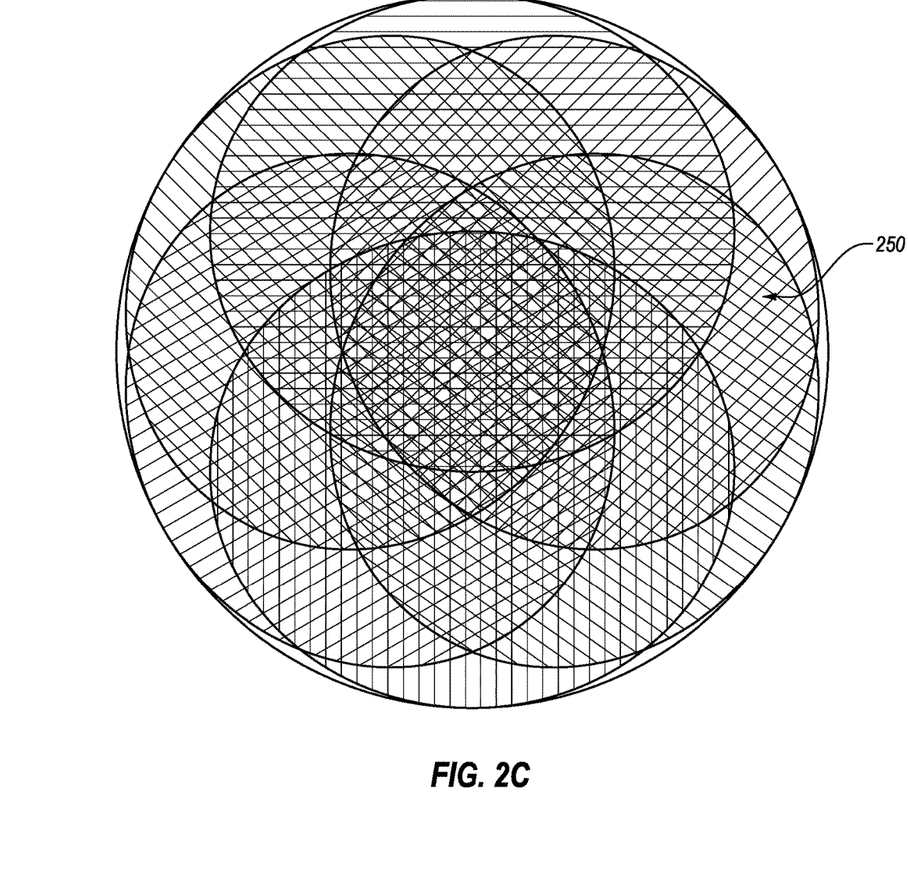
FIG. 2C illustrates a cross-sectional front view of the eye of FIG. 1A, including yet another example set of multiple overlapping imaging regions of the eye.

FIGS. 2A-2C illustrate a cross-sectional front view of the eye of FIG. 1A, including example sets of multiple overlapping imaging regions of the eye, all arranged according to one or more embodiments of the present disclosure. As illustrated, FIG. 2A depicts a first set of multiple overlapping imaging regions of the eye, including imaging regions 120*a*/120*b*/120*c* at a first position with scallops 205. As used herein, the term scallop or scallop-shaped region/area may refer to the unimaged region (e.g., 205) or the shape of the image proximate the unimaged region as caused by unimaged regions at the boundaries between the multiple overlapping imaging regions of the eye. In this example embodiment, the imaging regions 120*a*/120*b*/120*c* correspond to the retina 125, but in other embodiments, may correspond to other portions of the eye such as the cornea, the iris, the iridocorneal angle, the sclera, and any other suitable area of the eye, whether in the anterior or posterior chamber of the eye. FIG. 2A may be the same as or similar to FIG. 1C, with the additional label of the scallops 205. The scallops 205 may include a first set of un-imaged areas outside of the field of view of the image capturing devices. In these or other embodiments, the imaging regions 120*a*/120*b*/120*c* relative to the scallops 205 may be correspondingly imaged and a first composite image may be generated therefrom.

Then, according to FIG. 2B, the optical imaging device with multiple optical imaging pathways may be rotated such that the imaging regions 120a/120b/120c move to a different position, and new images may be acquired for generating a second composite image. Accordingly, after rotation of the optical imaging device, new scallops may be formed, e.g., scallops 210. The scallops 210 may include a second set of un-imaged areas outside of the field of view of the image capturing devices. In these or other embodiments, the scallops 210 may be positioned differently than the scallops 205. Additionally or alternatively, at least a portion of one of the scallops 205 may be included within one or more of the imaging regions 120a/120b/120c post-rotation of the optical imaging device. Additionally or alternatively, at least a portion of one of the scallops 210 may be included within one or more of the imaging regions 120a/120b/120c prior to rotation of the optical imaging device.

Then, according to FIG. 2C, the first and second composite images (e.g., of FIGS. 2A-2B, respectively) may be stitched into one super-montaged image 250 with reduced scalloped areas of exclusion from the super-montaged image 250. Additionally or alternatively, each of the individual images of the first and second composite images may be individually montaged into the super-montaged image 250 with reduced scalloped areas.

Additionally or alternatively, the super-montaged image 250 may be more rotationally symmetrical than were either of the first or second composite images individually. In these or other embodiments, as a number or size of scallops increases at an outer edge of a composite image, the less rotationally symmetrical the composite image may be. Additionally or alternatively, as the number or size of scallops decreases at the outer edge of the composite image, the more rotationally symmetrical the composite image may be. For example, as the super-montaged image 250 is iteratively improved upon with additional image acquisition and image stitching, the super-montaged image 250 may become more round, more complete, and/or more circular shaped. Additionally or alternatively, the optical imaging device may iteratively rotate and perform image acquisition and composite image stitching to generate higher quality images and/or a larger field of view of the eye. Additionally or alternatively, the optical imaging device may be configured to iteratively rotate and perform image acquisition and composite image stitching until a threshold amount of surface area of the eye is acquired and/or until a threshold resolution is attained. In these or other embodiments, the amount of increased surface area in the super-montaged image 250 may be determined based on an image comparison of any of the first composite image and the second composite image. For example, the image comparison may include optical landmarks and features as respectively depicted in the first composite image and the second composite image to quantitatively reference how much surface area is improved in the super-montaged image 250. As referred to herein, the terms "landmarks" and "features" may include any anatomical component of the eye (e.g., fovea), an area of the eye (e.g., trabecular meshwork, Schwalbe's line, etc.), or a potential defect (e.g., scleral spur, angle recess, etc.).

Modifications, additions, or omissions may be made to the embodiments of FIGS. 2A-2C without departing from the scope of the present disclosure. For example, in some embodiments, the imaging regions 120a/120b/120c may be differently sized and shaped, and/or include different portions of the retina 125 than may be explicitly illustrated or described.

FIG. 3 illustrates a cross-sectional front view of an optical imaging device 300 for imaging the eye, relative to facial features, all arranged according to one or more embodiments of the present disclosure. As illustrated, the optical imaging device 300 includes a support structure 302, lenses 305a-305c, imaging channels 313a-313c, and image capturing devices 355a-355c. In some embodiments, the optical imaging device 300 may be aligned relative to a central axis 110 of an eye. Additionally or alternatively, the lenses 305a-305c, the imaging channels 313a-313c, and the image capturing devices 355a-355c may be the same as or similar to the lenses 105a-105b, the imaging channels 113a-113b, and the image capturing devices 155a-155b, respectively, of FIG. 1B.

The support structure 302 may be the same as or similar to the support structure described in U.S. Provisional patent application Ser. No. 16/217,750 entitled MULTIPLE OFF-AXIS CHANNEL OPTICAL IMAGING DEVICE UTILIZING UPSIDE-DOWN PYRAMIDAL CONFIGURATION filed on Dec. 12, 2018, the contents of which are hereby incorporated by reference in their entirety. In these or other embodiments, the support structure 302 may house the lenses 305a-305c, the imaging channels 313a-313c, and the image capturing devices 355a-355c. Additionally or alternatively, the support structure 302 may be sized and shaped for ergonomic purposes, e.g., to more suitably interface with facial features of a patient. In other embodiments, additional configurations of the support structure 302, other than an upside-down pyramidal configuration, may be implemented. For example, any suitable configuration permitting additional or increased clearance between the support structure 302 and one or both of a bony brow and a nose is contemplated herein. Additionally or alternatively, any suitable configuration permitting multiple imaging channels 313, e.g., two or more imaging channels 313, for imaging the eye may be implemented. For example, the support structure 302 may take a frustoconical shape.

In some embodiments, the optical imaging device 300 may be rotated by rotating the support structure 302. For example, by rotating the support structure 302 in a clockwise or counter-clockwise direction about the central axis 110 of the eye, different portions of the eye may be imaged permitting the rotational montage technique described above in conjunction with FIGS. 2A-2C. Additionally or alternatively, one or more of the imaging channels 313 may be rotated relative to the support structure 302. For example, while the support structure 302 remains in a static position relative to the eye and/or facial features of the patient, any of the imaging channels 313 may be rotated inside the support structure 302. Such internal rotation of the imaging channels 313 may enable different portions of the eye to be imaged permitting the rotational montage technique described above in conjunction with FIGS. 2A-2C.

In some embodiments, more or fewer numbers of lenses 305 may be used within any of the imaging channels 313, e.g., to permit more suitable imaging of a particular area of the eye. Additionally or alternatively, the lenses 305 may be sized and shaped to fill an inner diameter of the imaging channels 313 that house the lenses 305, while in other embodiments, the lenses 305 may be sized and shaped to be less than the inner diameter of the imaging channel 313. Additionally or alternatively, one or more components may be positioned between, adjacent to, distal to, and/or proximal to any of the lenses 305.

In some embodiments, the imaging channels 313a-313c may be angled relative to each other. Additionally or alternatively, the imaging channels 313a-313c may be angled relative to the central axis 110 of the eye such that no imaging channel 313 may be coaxial with the central axis 110 of the eye. In other embodiments, at least one imaging channel 313 may be coaxial with the central axis 110 of the eye. The imaging channels 313a-313c may be sized, shaped and/or positioned within the support structure 302 in any suitable configuration, e.g., depending on an imaging application or pupil size of the eye to be imaged. Additionally or alternatively, the imaging channels 313a-313c may be sized, shaped and/or positioned relative to the eye, e.g., the central axis 110 of the eye depending on an imaging application or pupil size of the eye to be imaged.

Additionally or alternatively, more or fewer imaging channels 313 may be utilized in the optical imaging device 300, e.g., to facilitate up to three hundred and sixty degrees around the eye of image acquisition capability. For example, the optical imaging device 300 may include imaging channels 313 numbering between two and twelve imaging channels 313, such as between two and three, three and four, four and five, five and six, six and seven, seven and eight, eight and nine, or nine and ten. In some embodiments, more imaging channels 313 may be utilized to provide a more circumferential view of the eye while less imaging channels 313 may provide less of a circumferential view of the eye, given that each imaging channel 313 may only capture a portion of the eye. In these or other embodiments, the image capturing devices 355 may capture images all at the same time or in rapid succession, for example, using a rapid multi-plex. In this manner, for example, topographical information or a topographical profile may be generated at representative locations, e.g., at 12 o'clock, 2 o'clock, 4 o'clock, 6 o'clock, 8 o'clock, and 10 o'clock positions of the eye.

Modifications, additions, or omissions may be made to the embodiments of FIG. 3 without departing from the scope of the present disclosure. For example, in some embodiments, the support structure 302 may include any number of other components that may not be explicitly illustrated or described. Additionally or alternatively, the support structure 302 may be sized, shaped, and/or oriented relative to facial features in other suitable ways than may be explicitly illustrated or described. Additionally or alternatively, for example, the imaging channels 313a-313c may be sized, shaped, positioned, and/or oriented within the support structure 302 in other suitable ways than may be explicitly illustrated or described.

Figure 4:
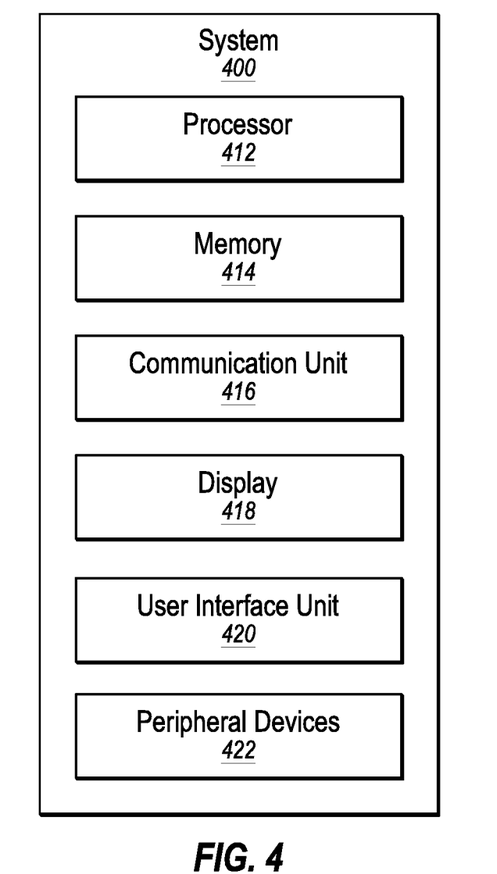
FIG. 4 illustrates an example system that may be used in multiple off-axis channel imaging of the eye.

FIG. 4 illustrates an example system 400 that may be used in multiple off-axis channel imaging of the eye. The system 400 may be arranged in accordance with at least one embodiment described in the present disclosure. The system 400 may include a processor 410, memory 412, a communication unit 416, a display 418, a user interface unit 420, and a peripheral device 422, which all may be communicatively coupled. In some embodiments, the system 400 may be part of any of the systems or devices described in this disclosure.

Generally, the processor 410 may include any suitable special-purpose or general-purpose computer, computing entity, or processing device including various computer hardware or software modules and may be configured to execute instructions stored on any applicable computer-readable storage media. For example, the processor 410 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data.

Although illustrated as a single processor in FIG. 4, it is understood that the processor 410 may include any number of processors distributed across any number of networks or physical locations that are configured to perform individually or collectively any number of operations described in this disclosure. In some embodiments, the processor 410 may interpret and/or execute program instructions and/or process data stored in the memory 412. In some embodiments, the processor 410 may execute the program instructions stored in the memory 412.

For example, in some embodiments, the processor 410 may execute program instructions stored in the memory 412 that are related to determining whether generated sensory data indicates an event and/or determining whether the event is sufficient to determine that the user is viewing a display of a device such that the system 400 may perform or direct the performance of the operations associated therewith as directed by the instructions. In these and other embodiments, instructions may be used to perform one or more operations or functions described in the present disclosure.

The memory 412 may include computer-readable storage media or one or more computer-readable storage mediums for carrying or having computer-executable instructions or data structures stored thereon. Such computer-readable storage media may be any available media that may be accessed by a general-purpose or special-purpose computer, such as the processor 410. By way of example, and not limitation, such computer-readable storage media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store particular program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause the processor 410 to perform a certain operation or group of operations as described in this disclosure. In these and other embodiments, the term "non-transitory" as explained in the present disclosure should be construed to exclude only those types of transitory media that were found to fall outside the scope of patentable subject matter in the Federal Circuit decision of In re Nuijten, 500 F.3d 1346 (Fed. Cir. 2007). Combinations of the above may also be included within the scope of computer-readable media.

The communication unit 416 may include any component, device, system, or combination thereof that is configured to transmit or receive information over a network. In some embodiments, the communication unit 416 may communicate with other devices at other locations, the same location, or even other components within the same system. For example, the communication unit 416 may include a modem, a network card (wireless or wired), an infrared communication device, a wireless communication device (such as an antenna), and/or chipset (such as a Bluetooth device, an 802.6 device (e.g., Metropolitan Area Network (MAN)), a Wi-Fi device, a WiMax device, cellular communication facilities, etc.), and/or the like. The communication unit 416 may permit data to be exchanged with a network and/or any other devices or systems described in the present disclosure.

The display 418 may be configured as one or more displays, like an LCD, LED, or other type of display. For example, the display 418 may be configured to present measurements, indicate warning notices, show tolerance ranges, display whether good/bad eye tissues are determined, and other data as directed by the processor 410.

The user interface unit 420 may include any device to allow a user to interface with the system 400. For example, the user interface unit 420 may include a mouse, a track pad, a keyboard, buttons, and/or a touchscreen, among other devices. The user interface unit 420 may receive input from a user and provide the input to the processor 410. In some embodiments, the user interface unit 420 and the display 418 may be combined.

The peripheral devices 422 may include one or more devices. For example, the peripheral devices may include a sensor, a microphone, and/or a speaker, among other peripheral devices. As examples, the sensor may be configured to sense changes in light, sound, motion, rotation, position, orientation, magnetization, acceleration, tilt, vibration, etc., e.g., as relating to an eye of a patient. Additionally or alternatively, the sensor may be part of or communicatively coupled to the optical imaging device as described in the present disclosure.

Modifications, additions, or omissions may be made to the system 400 without departing from the scope of the present disclosure. For example, in some embodiments, the system 400 may include any number of other components that may not be explicitly illustrated or described. Further, depending on certain implementations, the system 400 may not include one or more of the components illustrated and described.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner. Additionally, the term "about" or "approximately" should be interpreted to mean a value within 10% of actual value.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

What is claimed is:

1. An optical imaging device, comprising:
   a support structure;

a plurality of imaging channels, each imaging channel of the plurality of imaging channels including a discrete optical imaging pathway, the plurality of imaging channels disposed within the support structure, the plurality of imaging channels aimed at different angles relative to each other such that each optical imaging pathway is directed through a pupil of an eye towards corresponding partially overlapping regions of a retina; and a plurality of image capturing devices, each image capturing device of the plurality of image capturing devices respectively associated with one of the plurality of imaging channels to capture a first set of digital photograph images of respective portions of the eye, wherein the first set of digital photograph images overlap each other and are stored in a storage device of the optical imaging device for stitching together such that the first set of digital photograph images form a first composite image with a first plurality of scallop-shaped regions, wherein the optical imaging device is configured to be rotated to capture a second set of digital photograph images that overlap each other and are stored in the storage device of the optical imaging device for stitching together such that the second set of digital photograph images form a second composite image with a second plurality of scallop-shaped regions positioned differently than the first plurality of scallop-shaped regions, and wherein the optical imaging device is configured to stitch the first composite image and the second composite image together to form a third composite image, wherein the first composite image and the second composite image capture the eye such that when stitched together to form the third composite image, the third composite image includes a greater amount of imaged surface area of the eye than the first composite image or the second composite image individually.

2. The optical imaging device of claim 1, wherein the third composite image is shaped more rotationally symmetrical than either of the first composite image or the second composite image.

3. The optical imaging device of claim 1, wherein the greater amount of imaged surface area in the third composite image is based on an image comparison of optical landmarks and features between the first composite image and the second composite image.

4. The optical imaging device of claim 1, further comprising:
a plurality of sets of optical lenses, at least one lens in each of the sets of optical lenses having a fixed position within a respective imaging channel of the plurality of imaging channels.

5. The optical imaging device of claim 1, wherein the discrete optical imaging pathways of the plurality of imaging channels converge at a position inside a posterior cavity of the eye and anterior to an equatorial line of the eye.

6. The optical imaging device of claim 1, wherein each individual image comprising the first composite image and the second composite image are stored in the storage device of the optical imaging device for generation of a supermontage image using each individual image of the first composite image and the second composite image.

7. The optical imaging device of claim 1, wherein the optical imaging device is configured to repeatedly rotate for iterative, composite image acquisition that increases a field of view of the eye until a threshold amount of surface area of the eye is imaged.

8. The optical imaging device of claim 1, wherein the optical imaging device is configured to repeatedly rotate for iterative, composite image acquisition until a threshold resolution is obtained of the composite images.

9. The optical imaging device of claim 1, wherein:
at least a portion of one scallop-shaped region of the first plurality of scallop-shaped regions in the first composite image is included in the second composite image; and
at least a portion of one scallop-shaped region of the second plurality of scallop-shaped regions in the second composite image is included in the first composite image.

10. A system comprising:
one or more processors configured to receive optical imaging data; and
an optical imaging device configured to generate optical imaging data, the optical imaging device communicatively coupled to the one or more processors, and the optical imaging device comprising:
a support structure;
a plurality of imaging channels, each imaging channel of the plurality of imaging channels including a discrete optical imaging pathway, the plurality of imaging channels disposed within the support structure, the plurality of imaging channels aimed at different angles relative to each other such that each optical imaging pathway is directed through a pupil of an eye towards corresponding partially overlapping regions of a retina; and
a plurality of image capturing devices, each image capturing device of the plurality of image capturing devices respectively associated with one of the plurality of imaging channels to capture a first set of digital photograph images of respective portions of the eye, wherein the first set of digital photograph images overlap each other and are stored in a storage device of the optical imaging device for stitching together such that the first set of digital photograph images form a first composite image with a first plurality of scallop-shaped regions, wherein the optical imaging device is configured to be rotated to capture a second set of digital photograph images that overlap each other and are stored in the storage device of the optical imaging device for stitching together such that the second set of digital photograph images form a second composite image with a second plurality of scallop-shaped regions positioned differently than the first plurality of scallops, and wherein the one or more processors are configured to stitch the first composite image and the second composite together to form a third composite image, the third composite image including a greater amount of imaged surface area of the eye than the first composite image or the second composite image individually.

11. The system of claim 10, wherein the third composite image is shaped more rotationally symmetrical than either of the first composite image or the second composite image.

12. The system of claim 10, wherein the greater amount of imaged surface area in the third composite image is based on an image comparison of optical landmarks and features between the first composite image and the second composite image.

13. The system of claim 10, further comprising:
a plurality of sets of optical lenses, at least one lens in each of the sets of optical lenses having a variable position within a respective imaging channel of the plurality of imaging channels.

14. The system of claim 10, wherein the discrete optical imaging pathways of the plurality of imaging channels converge at a position inside a posterior cavity of the eye and anterior to an equatorial line of the eye.

15. The system of claim 10, wherein each individual image comprising the first composite image and the second composite image are stored in the storage device of the optical imaging device for generation of a super-montage image using each individual image of the first composite image and the second composite image.

16. The system of claim 10, wherein the optical imaging device is configured to repeatedly rotate for iterative, composite image acquisition that increases a field of view of the eye until a threshold amount of surface area of the eye is imaged.

17. The system of claim 10, wherein the optical imaging device is configured to repeatedly rotate for iterative, composite image acquisition until a threshold resolution is obtained of the composite images.

18. The system of claim 10, wherein:
at least a portion of one scallop-shaped region of the first plurality of scallop-shaped regions in the first composite image is included in the second composite image; and
at least a portion of one scallop-shaped region of the second plurality of scallop-shaped regions in the second composite image is included in the first composite image.

19. The optical imaging device of claim 1, further comprising one or more processors configured to stitch together the first composite image and the second composite image into the third composite image.

20. The optical imaging device of claim 19, wherein the one or more processors are remote from the plurality of image capturing devices.

* * * * *